(12) United States Patent
Ellmann et al.

(10) Patent No.: US 10,603,411 B2
(45) Date of Patent: Mar. 31, 2020

(54) PRODUCTION OF SEMIFINISHED GOODS FOR IMPLANTS BASED ON PLASTIC

(71) Applicant: R & K CAD/CAM TECHNOLOGIE GMBH & CO. KG, Berlin (DE)

(72) Inventors: Daniel Ellmann, Fredersdorf-Vogelsdorf (DE); Andreas Klar, Berlin (DE); Wolf-Dieter Müller, Berlin (DE); Andreas Schwitalla, Berlin (DE); Justus Lackmann, Wolfsburg (DE); Tobias Spintig, Berlin (DE); Mohamed Abou-Emara, Berlin (DE); Ilona Kallage, Berlin (DE)

(73) Assignee: R + K CAD/CAM TECHNOLOGIE GMBH & CO. KG, Berlin (DE)

( * ) Notice: Subject to any disclaimer, the term of this patent is extended or adjusted under 35 U.S.C. 154(b) by 0 days.

(21) Appl. No.: 14/898,335

(22) PCT Filed: Jun. 16, 2014

(86) PCT No.: PCT/EP2014/001629
§ 371 (c)(1),
(2) Date: Dec. 14, 2015

(87) PCT Pub. No.: WO2014/198421
PCT Pub. Date: Dec. 18, 2014

(65) Prior Publication Data
US 2016/0206786 A1     Jul. 21, 2016

(30) Foreign Application Priority Data

Jun. 14, 2013   (DE) .................. 10 2013 211 175

(51) Int. Cl.
*A61L 27/48* (2006.01)
*A61L 27/06* (2006.01)
(Continued)

(52) U.S. Cl.
CPC ............. *A61L 27/443* (2013.01); *A61L 27/06* (2013.01); *A61L 27/08* (2013.01); *A61L 27/18* (2013.01);
(Continued)

(58) Field of Classification Search
None
See application file for complete search history.

(56) References Cited

U.S. PATENT DOCUMENTS

| | | | |
|---|---|---|---|
| 6,193,516 B1 * | 2/2001 | Story .................. | A61C 8/0086 433/173 |
| 2007/0111165 A1 * | 5/2007 | Wallick ................ | A61C 8/0012 433/212.1 |

(Continued)

FOREIGN PATENT DOCUMENTS

| | | |
|---|---|---|
| CN | 101904777 A | 12/2010 |
| FR | 2915088 | 10/2008 |

OTHER PUBLICATIONS

Elastic modulus and hardness of cortical and trabecular bone lamellae measured by nanoindentation in the human femur, Zysset et al, Journal of Biomechanics 32 (1999) 1005-1012.*
Espacenet—Cited documents for CN105705174 (A); Jun. 22, 2016.

*Primary Examiner* — Peter A Salamon
(74) *Attorney, Agent, or Firm* — Preti Flaherty Beliveau & Pachios LLP (57) ABSTRACT

The invention relates to an implant preform made of plastic, which comprises an assembly of at least one biocompatible—being intended for contact with a biological material—thermoplastic plastics unit (A) having an elasticity modulus $E_A$ and at least one thermoplastic plastics unit (B) having an elasticity modulus $E_B$, where for the elasticity moduli of these plastics units $E_A < E_B$, and the plastics units in their assembly zone are seamlessly connected thermally to one another. The invention also relates to the production (Continued)

of the implant preform made of plastic and also to the use of the implant preform as an implant or for fabrication of an implant therefrom, more particularly to the use thereof as a dental implant or for fabrication of a dental implant. The invention can also be applied to other bone implants.

34 Claims, 4 Drawing Sheets (51) Int. Cl.
    *A61L 27/08*     (2006.01)
    *A61L 27/18*     (2006.01)
    *A61L 27/50*     (2006.01)
    *C08L 71/12*     (2006.01)
    *A61L 27/44*     (2006.01)

(52) U.S. Cl.
    CPC .............. *A61L 27/446* (2013.01); *A61L 27/48* (2013.01); *A61L 27/50* (2013.01); *A61L 2430/12* (2013.01)

(56) References Cited

U.S. PATENT DOCUMENTS

2009/0222091 A1*   9/2009   Morrissette ............. A61L 27/18
                                                                       623/17.11
2010/0312348 A1   12/2010   Wang et al.

* cited by examiner

PRODUCTION OF SEMIFINISHED GOODS FOR IMPLANTS BASED ON PLASTIC

The invention relates to an implant preform made of plastic, to its production, and to the use of the implant preform as an implant or for fabrication of an implant therefrom, more particularly to the use thereof as a dental implant or for fabrication of a dental implant.

An implant is an artificial material which is implanted in the body and is intended to remain there permanently or at least for a prolonged period. In human medicine, implants are employed when disease, wear, or traumatic damage means that a natural tissue or natural material, such as, for example, teeth, bones, joints, and so on, is no longer able to fulfill its function.

In the sector of dental medicine, dental implants are used in the jawbone, and take on the function of an artificial tooth root. This system is generally composed of two parts: the implant, which is implanted in the jawbone, and an abutment, which joins the artificial replacement tooth to the implant.

Implants used generally in the human body are nowadays produced using various materials from the groups of the metals, ceramics, and plastics. They all share approval for long-term implantation on the basis of their proven biocompatibility.

The high mechanical requirements imposed on implants which are anchored in bony structures of the human skeleton require them to have correspondingly high elasticity moduli and also corresponding stability. Employed, therefore, to date here were primarily titanium and alloys of titanium, and also ceramics.

Titanium, and especially zirconium oxide, feature high strength and only very low physical elasticity. The elasticity moduli of titanium and of zirconium oxide are 105 and 200 kN/mm$^2$, respectively. If the prosthetic material or implant consists of one of these materials, the forces which act on the superstructure (prosthetic) during mastication are transmitted via the abutment post directly into the implant and from there to the jawbone. This rigid structure is not in accordance with the natural, elastic suspension of the tooth in the jaw.

Where the materials of an implant are too stiff for the bone, however, this is manifested in what is called the "stress shielding" effect. "Stress shielding" is understood as a reduction in bone density owing to the absence of the normal stress in the bone as a result of an implant, as for example of a femoral component of a hip prosthesis, or a maxillary or dental implant. It is known that under normal conditions the bone is built up and increases in strength when it is loaded. Accordingly, the bone adapts in its shape to the function, whereas under long-term absence of load—i.e., the bone is unloaded or receives only a low load—the bone degenerates or breaks down. The changing of a bone therefore follows the forces which act on the bone, and the mechanical forces constitute the basis for the perfect architecture of bone substance and bone structures. Comparable effects are applicable in the case of dental implants too.

If, therefore, the materials used for an implant, as for example for a dental implant, are too stiff for the bone, and if, accordingly, there is an absence of the stimulation required for the maintenance and adaptation of the bone substance, the bone loses bone mass in the region of the implant, owing to the shielding from physiological loading by the implant, and loses density and strength.

Recently, therefore, high-performance plastics, such as polyetheretherketone (PEEK), for example, have been making inroads in this territory, since they have an elasticity modulus (e-modulus) similar to that of bony tissue, and so the bone continues to experience the physiological loading, so as not to lose stability. Accordingly, these high-performance plastics, especially PEEK, appear to represent the material of choice for the production of implants, especially of dental implants.

It is often necessary, however, to reinforce these high-performance plastics by means of additions, in order to meet particular mechanical requirements in practice. Accordingly, many implants, such as osteosynthesis plates and especially dental implants, for example, are fixed by screws, with dental implants, for example, having a special central internal thread to allow an abutment post, on which the artificial replacement tooth can in turn be fixed, to be screwed firmly in the dental implant. An internal thread of this kind must be fabricated from a material which is able to withstand very high mechanical stresses imposed by the screw that is introduced. Suitable reinforced high-performance plastics are fiber-reinforced, an example being fiber-reinforced PEEK such as, in particular, carbon fiber-filled PEEK. These fiber-reinforced plastics materials, which are vital as a core material for an implant, especially a dental implant, inevitably, however, have an elasticity modulus which is very much greater than the elasticity modulus of bone, which is situated in the range from about 18 to 21 kN/mm$^2$. Even with these reinforced plastics materials, therefore, the problem of the above-described stress shielding effect may occur.

The object, therefore, was to specify implant preforms made of plastic, and their production, that do not exhibit the aforementioned disadvantages of the prior art and are suitable for use as an implant or for fabrication of an implant therefrom, more particularly for use as a dental implant or for fabrication of a dental implant. These implant performs made of plastic are to avoid stress shielding effects to as great an extent as possible, and are to have sufficiently high mechanical strength in order to ensure fastening that is secure—that is, for example, is durable and is up to exacting mechanical demands—of further implant components, by means of screwing, for example.

The object is achieved by the implant preform of the invention, made of plastic and described below, by its production and by the use of the implant preform as an implant or for fabrication of an implant therefrom, more particularly its use as a dental implant or for fabrication of a dental implant. The achievement of the invention is also suitable, furthermore, generally for the provision and use of implant preforms as a basis for elimination of diverse bone defects, or for reconstruction of bones, or for fabrication of a bone implant in order to eliminate bone defects. The invention, therefore, also relates to such bone implants, especially as an implant plate for reconstruction of bone or for elimination of bone defects, or for the fabrication of an implant plate of this kind.

In accordance with the invention it has now been found that when using plastics materials having a high elasticity modulus, which is greater, more particularly very much greater, than the elasticity modulus of bone, it is possible nevertheless for a stress shielding effect to be very largely, or even entirely, avoided if these plastics materials (B) are equipped suitably and seamlessly with a plastics material (A) that is biocompatible—being intended for contact with the biological material, as for example for contact with bone substance—and that has a lower elasticity modulus than that of the plastics material (B). In particular here, the elasticity modulus of the biocompatible plastics material (A) is similar to the elasticity modulus of bone.

In a first embodiment, therefore, the invention relates to an implant preform of plastic that is distinguished by the fact that it comprises an assembly of at least one biocompatible—being intended for contact with a biological material—(first) thermoplastic plastics unit (A) having an elasticity modulus $E_A$ and at least one (second) thermoplastic plastics unit (B) having an elasticity modulus $E_B$, where for the elasticity moduli of these plastics units $E_A < E_B$, and the plastics units in their assembly zone are seamlessly connected thermally to one another.

A preform is understood in the sense of the invention to refer to prefabricated raw material shapes for bone implants, for example, such as generally for bone implants for reconstruction of bone or for eliminating bone defects, for example, and especially for dental implants, that are made of plastic and that are intermediates (semifabricated or semifinished products), produced to a state of partial readiness in each case in terms of grade of material and surface quality, shape and dimensions, and also in terms of their tolerances, and which are generally standardized, and which can be produced to a state of readiness for the definitive end use in a subsequent processing operation. The preforms here, as semifabricated or semifinished products, are generally designed in such a way that in terms of shape and dimensions they correspond as ideally as possible to the product that is to be produced—for example, to the implant, and especially to the dental implant. The material grades and surface qualities are judiciously optimized for the particular end use and for the fabrication process. The same applies, analogously, to other bone implants.

Elasticity refers to the property of a body or a material, particularly in the context of its use as intended, to react reversibly to a force acting on it. Elasticity in the sense of the invention is therefore the property displayed by the implant preform or implants produced from it, more particularly dental implants, of changing its shape on exposure to force and returning to the original shape on removal of the acting force. For the implant preform and the implants produced from it, the elasticity corresponds essentially to natural elastic conditions of the bone; in other words, particularly in the context of dental implants, the elasticity corresponds essentially to the natural elastic suspension of the tooth in the jaw.

In order to be able to treat the elasticity as a parameter for particular end uses of materials, the elasticity of materials is described in detail by the elasticity modulus (expressed in $kN/mm^2$), the compression modulus, and the shear modulus. These moduli are linked with one another via the Poisson number.

The elasticity modulus here describes the correlation between stress and strain in the deformation of a solid body in the case of linear elastic behavior. The compression modulus is used to calculate which all-round pressure change is necessary in order to bring about a defined reversible volume change. The shear modulus provides information on the linear elastic deformation of a component as a consequence of a shearing force or shear stress.

For the purposes of the invention, particular importance attaches to the elasticity modulus (expressed in $kN/mm^2$). In a second embodiment, therefore, the invention relates to an implant preform made of plastic that is distinguished by the fact that it comprises an assembly of at least one biocompatible—being intended for contact with a biological material—(first) thermoplastic plastics unit (A) having an elasticity modulus $E_A$ and at least one (second) thermoplastic plastics unit (B) having an elasticity modulus $E_B$, where for the elasticity moduli of these plastics units $E_A < E_B$, and the plastics units are seamlessly connected thermally to one another in their assembly zone in such a way that within the assembly zone there is a gradient from the elasticity modulus $E_B$ of the plastics unit (material B) to the elasticity modulus $E_A$ of the plastics unit (material A).

The assembly zone, i.e. the seamless transition between the thermoplastic plastics unit (A) and a thermoplastic plastics unit (B), can have a wholly or partly smooth and/or interlocking design. The assembly zone, whose cross section can be investigated microscopically, for example, is in general up to about 2 mm wide, and protrudes in each case up to about 1 mm, from the interface of the plastics units, into the thermoplastic plastics unit (A) and the thermoplastic plastics unit (B). The assembly zone may also, for example, be only up to about 1 mm wide, or may protrude from the interface only up to about 0.5 mm into, in each case, the thermoplastic plastics unit (A) and the thermoplastic plastics unit (B). More particularly, the assembly zone may also be only 0.5 mm wide, or then protrude from the interface only up to about 0.25 mm into, in each case, the thermoplastic plastics unit (A) and the thermoplastic plastics unit (B).

A gradient in the sense of the present invention refers to the elasticity modulus as a directed physical variable (elasticity modulus gradient), and describes, in the assembly zone of the thermoplastic plastics unit (A) and the thermoplastic plastics unit (B), a gradient in the values of the elasticity modulus ($kN/mm^2$) from the higher elasticity modulus $E_B$ of the thermoplastic plastics unit (B) to the lower elasticity modulus $E_A$ of the thermoplastic plastics unit (A).

One judicious embodiment of the implant preform of the invention is distinguished by the fact that the elasticity modulus $E_A$ of the thermoplastic plastics unit (A) is about 1 to 6 GPa, preferably about 2 to 5 GPa, more preferably about 2.5 to 4.5 GPa.

One judicious embodiment of the implant preform of the invention is distinguished by the fact that the elasticity modulus $E_B$ of the thermoplastic plastics unit (B) is 5 to 160 GPa, preferably 20 to 150 GPa, more preferably 30 to 110 GPa.

In further judicious embodiments of the implant preform of the invention, they are distinguished by the fact that the ratio of the elasticity modulus $E_A$ of the thermoplastic plastics unit (A) to the elasticity modulus $E_B$ of the thermoplastic plastics unit (B) is $E_A < 1.1\ E_B$, and preferably $E_A < 1.5\ E_B$. In particularly judicious embodiments, the ratio of the elasticity modulus $E_A$ of the thermoplastic plastics unit (A) to the elasticity modulus $E_B$ of the thermoplastic plastics unit (B) is $E_A < 1.1$ to $50\ E_B$, and preferably $E_A < 1.5$ to $50\ E_B$. In a further embodiment, the ratio of the elasticity modulus $E_A$ of the thermoplastic plastics unit (A) to the elasticity modulus $E_B$ of the thermoplastic plastics unit (B) can be $E_A < 5$ to $44\ E_B$.

In the embodiments of the invention, as for example in the implant preform or an implant produced therefrom, the plastics unit (A) intended for contact with a biological material, i.e., in particular, for contact with bone, may also be designed as external, and the plastics unit (B) may also be designed as internal. The plastics unit (A) may then preferably form a shell or a jacket, with the plastics unit (B) then forming a core or a cylinder which is surrounded by or inlaid into this shell or this jacket of the plastics unit (A). Correspondingly, the material of the plastics unit (A) may also be referred to as shell material or jacket material, and the material of the plastics unit (B) may also be referred to as core material.

In a first variant of this embodiment, therefore, the invention relates to an implant preform made of plastic, which is distinguished by the fact that it comprises an assembly of at least one biocompatible—being intended for contact with a biological material—external (first) thermoplastic plastics unit (A), designed preferably as a shell or as a jacket and having an elasticity modulus $E_A$, and at least one internal, (second) thermoplastic plastics unit (B), designed preferably as a core and having an elasticity modulus $E_B$, where for the elasticity moduli of these plastics units $E_A < E_B$, and the plastics units in their assembly zone are joined seamlessly to one another thermally.

In a second variant of this embodiment, therefore, the invention relates to an implant preform made of plastic, which is distinguished by the fact that it comprises an assembly of at least one biocompatible—being intended for contact with a biological material—external (first) thermoplastic plastics unit (A), designed preferably as a shell or as a jacket and having an elasticity modulus $E_A$, and at least one internal, (second) thermoplastic plastics unit (B), designed preferably as a core and having an elasticity modulus $E_B$, where for the elasticity moduli of these plastics units $E_A < E_B$, and the plastics units in their assembly zone are joined seamlessly to one another thermally in such a way that in the assembly zone there is a gradient from the elasticity modulus $E_B$ of the plastics unit (material B) to the elasticity modulus $E_A$ of the plastics unit (material A).

In the implant preform of the invention the plastic in one or more of the plastics units, in each case independently of one another, is a biocompatible plastic, preferably a biocompatible high-performance thermoplastic.

An implant material is an inanimate material which is used for a medical application and which interacts with biological systems. Fundamental requirements for use of a material as implant material, in contact with the body environment in the case of definitive purpose, is its body compatibility (biocompatibility). Biocompatibility is understood as the capacity of a material to evoke an appropriate tissue response in a specific application. This includes adaptation of the properties of an implant material to the biological material with which it is in contact, with the objective of a clinically desired interaction. For the purposes of the invention, accordingly, the term "biocompatible" refers to a biological compatibility and acceptance of a material, as for example a plastics material for an implant preform of the invention, with living material—for example, in the context of the invention, in particular with bone tissue, but also with mucosa or, optionally, other tissues which come into contact with the material.

In one embodiment the implant preform of the invention is distinguished by the fact that the plastic in one or more of the plastics units, in each case independently of one another, is selected from the group of PEEK, PA, PE, POM, PMMA, PVAc, PU, PAEK; preferably PEEK or polymer blends or plastics blends thereof or based thereon.

In one embodiment the implant preform of the invention is distinguished by the fact that the plastic of the thermoplastic plastics unit (A) is selected from the group of PEEK, PA, PE, POM, PMMA, PVAc, PU, PAEK; preferably PEEK or polymer blends or plastics blends thereof or based thereon.

In one embodiment the implant preform of the invention is distinguished by the fact that the plastic of the thermoplastic plastics unit (B) is selected from the group of PEEK, or polymer blends or plastics blends thereof or based thereon.

In the implant preform of the invention the plastic in one or more of the plastics units, in each case independently of one another, may also be a polymer blend or plastics blend of two or more plastics, more particularly of two or more biocompatible plastics, preferably of two or more biocompatible high-performance thermoplastics. Polymer blends of this kind may be formed, for example, from the aforementioned plastics selected from the group of PEEK, PA, PE, POM, PMMA, PVAc, PU, PAEK or else polymer blends or plastics blends of one or more of these plastics with one or more other polymers or plastics, particularly other biocompatible polymers or plastics. Plastics blends of the thermoplastic plastics unit (A) are based judiciously on plastics selected from the group of PEEK, PA, PE, POM, PMMA, PVAc, PU, PAEK. Plastics blends of the thermoplastic plastics unit (B) are based judiciously on plastics selected from the group of PEEK or other thermoplastics such as PA, PE, POM, PMMA, PVAc, PU, PAEK. With preference such plastics blends of the plastics units (A) and (B), in each case independently of one another, are formed on the basis of PEEK.

In the implant preform of the invention, the plastic in one or more of the plastics units, in each case independently of one another, may also be a "compounded" plastic ("compound"), more particularly a "compounded" biocompatible plastic, preferably a "compounded" biocompatible high-performance thermoplastic.

The term "compounded" or "compound" (representing compounded substance, composition, or mixture) is understood for the purposes of the invention to refer to plastics that have been admixed with additional base materials such as fillers, reinforcing agents, or other adjuvants. As a result of the compounding, therefore, the plastics are bonded together with at least one base material to form a homogeneous mixture. The objective of compounding is to modify the properties of the plastics for a particular application by virtue of the base materials added. In particular, for the purposes of the present invention, base materials added to the plastics may judiciously be those which are biologically tolerated, i.e., biocompatible.

The process of producing a compound is called compounding. Compounding is therefore an operation for enhancement of plastics by admixing of additaments (fillers, reinforcing agents, adjuvants, etc.) for the targeted optimization of the profiles of properties of plastics. Compounding takes place primarily in extruders (principally corotating twin-screw extruders, but also contrarotating twin-screw extruders, and also by means of planetary roller extruders and cokneaders), and embraces, for example, process operations such as conveying, melting, dispersing, mixing, degassing, and development of pressure. In the case of thermoplastics, the compounding may be accomplished, for example, by means of twin-screw extruders.

The objectives of compounding are diverse and are guided by the desired properties of the subsequent plastics component. The most important objectives of the compounding in the context of the invention are for example as follows:

The modification of the mechanical properties of the base polymer. In this context, mechanical parameters such as the tensile strength and the impact strength are adjusted via the addition of reinforcing agents and fillers, and also via impact modification. Influencing the elasticity modulus is of particular importance in the context of the invention.

Color settings: The customer's desired color is set by the addition of pigments or what are called masterbatches. It may be necessary to consider the possibility of certain color settings influencing the mechanical properties.

Addition of processing aids: This group of substances essentially improves the processing of the polymers. In this way, for example, demolding in an injection molding operation is simplified by means of mold release assistants.

Adjuvants, also called auxiliaries or additives, are substances added in small amounts to plastics in order to attain or to improve or to modify certain properties. Adjuvants are used in order to achieve a positive effect on production, storage, processing, or on product properties during and after the service phase. Adjuvants are generally optimized for the particular application.

The invention therefore also relates to implant preforms which are distinguished by the fact that the plastic in one or more of the plastics units, in each case independently of one another, is an additized plastic, in other words a compounded or composite plastic. Such additives may be selected in the context of the invention, for example, from the following: reinforcing agents such as fibers, examples being carbon fibers, glass fibers; fillers such as, for example, $SiO_2$, $BaSO_4$, tricalcium phosphate, tetracalcium phosphate, and bioglasses (absorbable and/or stable calcium phosphate ceramics such as, for example, GB9, GB14, AP40); pigments such as $TiO_2$.

The invention in one embodiment relates to implant preforms which are distinguished in particular by the fact that the plastic of the thermoplastic plastics unit (A) comprises additives in powder form, preferably additives in powder form selected from the group of hydroxylapatite, tricalcium phosphate, tetracalcium phosphate, barium sulfate, titanium dioxide, zinc oxide, and bioglasses (absorbable and/or stable calcium phosphate ceramics such as, for example, GB9, GB14, AP40).

The invention in one embodiment relates to implant preforms which are distinguished in particular by the fact that the plastic of the thermoplastic plastics unit (B) is fiber-reinforced, e.g., glass fiber- and/or carbon fiber-reinforced, preferably carbon fiber-reinforced.

As already observed, the compounding in the context of the invention is important for influencing or purposively setting the elasticity modulus of the plastics units (A) and (B), in each case independently of one another. This is illustrated by way of example on the basis of the overview below, of various medically employable PEEK grades each with and without added base materials, such as fillers (powder) or reinforcing agents (fibers), for example, and with the respective elasticity modulus (E1-E8, as defined here below), which may be employed as plastics material (A), (B) and optionally as further plastics materials (C, D, etc.) for producing an implant preform of the invention.

PEEK unfilled/raw: elasticity modulus E1=1-4 GPa;
PEEK with powder from the group of titanium dioxide, barium sulfate, tricalcium phosphate, hydroxylapatite: elasticity modulus E2=1-6 GPa;
PEEK with glass fibers: short/chopped with elasticity modulus E3=5-20 GPa; continuous/unoriented with elasticity modulus E4=20-80 GPa; continuous/oriented with elasticity modulus E5=50-160 GPa;
PEEK with carbon fibers: short/chopped with elasticity modulus E6=5-20 GPa; continuous/unoriented with elasticity modulus E7=20-80 GPa; continuous/oriented with elasticity modulus E8=50-160 GPa.

The invention also relates to the production of implant preforms of the invention by means of suitable joining methods. Joining or joining methods are used in fabrication technology to refer to methods which connect two components durably to one another. For plastics, those used predominantly in the prior art are a thermal joining technique, as for example welding or friction welding, and adhesive bonding.

Various methods are suitable for producing an implant preform of the invention from two or more different thermoplastics (A) and (B), these being joining methods, which involve the thermoplastic plastics units (A) and (B) being brought together with sufficient formation of heat at the interface or in the assembly zone which forms in the thermoplastic plastics units (A) and (B).

A thermal joining method, as for example welding or friction welding, of plastics presupposes a capacity to form a melt. For this method, accordingly, only thermoplastics are suitable. The heat for the melting of the material may be supplied by means of electrical induction heating (heating element welding), hot compressed air (hot gas welding), friction of the molecules relative to one another (high-frequency welding), light or laser radiation (radiative welding), or friction (friction welding).

The desired durable connection of two different plastics parts (A) and (B) may hence be achieved in accordance with the invention through the introduction of energy in the form of heat, by friction, by heat treatment in an oven, by local application of heat, generated by hot air or LASER, or by melt in the case of injection overmolding. Methods which can be employed in accordance with the invention, joining methods for example, may be as follows, for example: a method by application of or, in particular, overmolding of the thermoplastic plastics unit (B) with the thermoplastic plastics unit (A) in an injection molding process or by extrusion; a method by means of laser sintering of the thermoplastic plastics unit (B) with the thermoplastics plastic unit (A); or a method by means of frictional welding of the thermoplastic plastics unit (B) with the thermoplastic plastics unit (A). The method for frictional welding of the thermoplastic plastics unit (B) to the thermoplastic plastics unit (A) is particularly preferred.

In one embodiment the invention therefore relates to a method for producing an implant preform of the invention made from plastic, as described above, which is distinguished by the fact that at least one biocompatible—being intended for contact with a biological material—(first) thermoplastic plastics unit (A) having an elasticity modulus $E_A$ and at least one (second) thermoplastic plastics unit (B) having an elasticity modulus $E_B$, where for the elasticity moduli of these plastics units $E_A < E_B$, are joined seamlessly to one another to form an assembly by a thermal joining technique, preferably by friction welding.

In a preferred embodiment, therefore, the invention relates to a method for producing a preferred implant preform of the invention made of plastic, as described above, said method being distinguished by the fact that the plastics units (A) and (B) are joined seamlessly to one another to form an assembly in such a way that in the assembly zone a gradient is set from the elasticity modulus $E_B$ of the (second) plastics unit (B) (material B) to the elasticity modulus $E_A$ of the (first) plastics unit (A) (material A).

The invention also relates to the use of the above-described implant preforms of the invention as an implant, more particularly as a bone implant, or for fabrication of an implant, preferably for fabrication of a bone implant. All kinds of bone implants are contemplated here, examples being implants for hip bones, cranial bones and/or jawbones. The implant preforms of the invention preferably find use as a dental implant or for fabricating a dental implant. To a person skilled in the art it is self-evident that all general and specific observations in relation to the above-described implant preforms of the invention apply equally, and can be used, for the inventive use of the implant preforms. The implant preforms of the invention may be used in a conventional way in accordance with the relevant methods known to the person skilled in the art.

The invention relates, furthermore, to the aforementioned implants themselves as well, especially in the form of bone implants which comprise an implant preform of the invention processed thereto. The implants of the invention here embrace all kinds of bone implants, examples being implants for hip bones, cranial bones and/or jawbones. The implants of the invention are preferably dental implants. It is self-evident to a person skilled in the art that all general and specific observations in relation to the above-described implant preforms of the invention and their use apply equally, and can be used equally, for the implants of the invention and their use. The further processing of the implant preforms of the invention to implants, or the production of implants, of the invention, and the use thereof, may take place in a conventional way in accordance with the relevant methods known to a person skilled in the art.

The invention is elucidated in more detail below by means of working examples relating to a preform as a basis for a dental implant and also as a basis for an implant plate for reconstruction of bone defects, and with reference to FIG. 1 to FIG. 4 of the figures.

ABBREVIATION INDEX

PA=polyamide; PE=polyethylene; PEEK=polyetheretherketone; PAEK=polyaryletherketone; PMMA=polymethyl methacrylate; PU=polyurethane; POM=polyoxymethylene; LASER=light amplification by stimulated emission of radiation; e-modulus=elasticity modulus; FE=finite elements; CAD=computer aided design; CAM=computer aided manufacturing.

Bone Implants, More Particularly Dental Implants

In the text below, the plastics unit (A) is also referred to as shell, jacket, or shell material or jacket material, and the plastics unit (B) also as core or core material.

Materials such as fiber-reinforced plastics, an example being carbon fiber-reinforced PEEK, do have an elasticity modulus which is very much greater than the elasticity modulus of bone, but are unavoidable for plastics material-based implants, particularly as core material for dental implants. In order to avoid the problem of the above-described stress shielding effect occurring in the case of these reinforced plastics materials, the application of a specific jacket layer onto the core material has been developed with the present invention, this jacket layer consisting of a plastics material having a modulus of elasticity similar to that of bone, and so functioning as a buffer zone between hard core material and bone. At the same time this jacket layer, which has a light color, fulfills an esthetic function, by visually shielding the core material, if the latter is filled with carbon fibers and therefore appears black, this being significant in particular in the context of dental implants, since they are in some cases visible within the oral cavity.

Biocompatible materials are employed which possess an elasticity modulus of up to 160 kN/mm$^2$ and more particularly less than 100 kN/mm$^2$. Such materials are, in particular, glass and carbon fiber-reinforced plastic and polyetheretherketone (PEEK), and materials with a higher elasticity modulus are of preferential suitability as core material, while materials with a lower elasticity modulus are of preferential suitability as shell material. These materials have elasticity moduli in the range of 3.7 kN/mm$^2$ (PEEK) and 40 kN/mm$^2$ (CRP in fiber direction). They are therefore substantially more resilient than titanium and zirconium oxide with an elasticity modulus of 105 and 200 kN/mm$^2$, respectively.

With regard both to ease of producibility and to a desired flexible capacity for adaptation to anatomical circumstances, it is preferred for the implant to be of monoblock construction. A preferred material is plastic, more particularly a material made of or based on polyamide or polyetherketone such as preferably made of polyetheretherketone (PEEK), or made of polyoxymethylene (e.g., Delrin), or the like. Polyetheretherketone (PEEK) particularly is able by virtue of its elasticity modulus to conform very well to the elasticity modulus of the jawbone.

For the core element of the dental implant it is possible in principle to produce plastics, such as PEEK, for example, in compounded form, in other words a homogeneous mixture of adjuvants and polymer matrix, in order to achieve different physical properties by virtue of the additives incorporated, fillers and/or fibers for example. In the case of this conventional compounding, the whole material thus produced is machined, with homogeneous commixing of the plastic with each of the incorporated additives. Where such materials, in the form of implants, for example, are employed in contact with human bone durably, it is also necessary to take account of the fact that bone tissue not only has a lower elasticity modulus than the majority of implants but also represents a material having regions of local difference in elasticity. In accordance with the invention, this fact is respected by the joining of two or more thermoplastics (e.g., PA, PU, PE, PAEK, PEEK) or two or more different compounds of a plastic to one another, the different elastic properties and elasticity moduli of the individual components giving rise to a new implant preform with locally modifiable and targetedly adjustable elastic properties and/or with an elasticity modulus gradient, primarily for medical application.

The core element here comprises combinations of plastics materials, primarily PEEK, having graded elastic properties in order to produce medically employable structures having a graduated stiffness in cross section; with graduated elasticity lengthwise, crosswise, locally distributed; and/or with variable hardness at the surface.

The desired durable connection of two different plastics parts is generated by introduction of energy in the form of heat, by friction, by heat treatment in an oven, by local application of heat by hot air or LASER, or by melt in the case of overmolding. In this way it is possible to fabricate dental implants or else other implant structures which remain durably in the human body and which are also able to accept a screw thread with fixing screw.

As a result of the invention, optimization of the mechanical properties at the site of application, of the color design, i.e., of the tooth colors, of the handling and durability, and also of the biological contact area, is achieved.

Combinations may in addition to pure PEEK combinations also be combinations of different plastics such as PMMA and PEEK, PA and PEEK, or HDPE and PEEK, provided that biocompatibility is ensured. Possible PEEK variants employed have been listed and elucidated in the description section above.

In order to produce a preform from two or more differently compounded thermoplastics, there are various suitable methods, such as, for example, overmolding in an injection molding process/extrusion, laser sintering, frictional welding.

In the text below, the production of a preform from two differently compounded PEEK grades is illustrated using frictional welding as an example. Unless otherwise indicated, % figures should be understood as wt %.

Production of a Dental Implant by Friction

The method of frictional welding, as an example of the production of a preform from at least two different thermoplastics, preferably PEEK grades, is based on the principle that by means of friction it is possible to ensure an appropriately high energy input with a maximum, at the interfaces of the two thermoplastics to be welded, that lies above the respective melting points of the materials to be welded and results in each of the surfaces rubbed against one another being partially melted, which then leads to a strong welded connection between the two thermoplastics.

In the present case, the heat energy required for welding is generated by means of rotational movements about the axis of a rotationally symmetrical plastics part (B) (material B) with continual pressing of the plastics part (B) (material B) against a plastics part (A) (material A), with material B representing the core material and material A representing the jacket material. For this purpose material B is introduced under pressure into a cylindrical hollow made beforehand in the material A by drilling, the drilled hole being smaller in diameter by 0.1-10%, preferably 5%, than the diameter of the cross-sectionally circular material B, in order to ensure a primary press fit between the two materials.

Subsequently, under a continual vertical pressure of 10-100 N, preferably 50 N, which acts over the longitudinal axis of the material B against A, the material B is rotated about its longitudinal axis within the drilled hole located in the material A, with a rotary speed of 200-1500 rpm, here preferably 300 rpm, for 0.5-5 seconds, here preferably 1 second. The resultant weld between the two materials has to cool at room temperature after the rotational movements have been shut off, with the vertical pressure being maintained, cooling taking place preferably over a period of at least 20 minutes.

Figure 1:
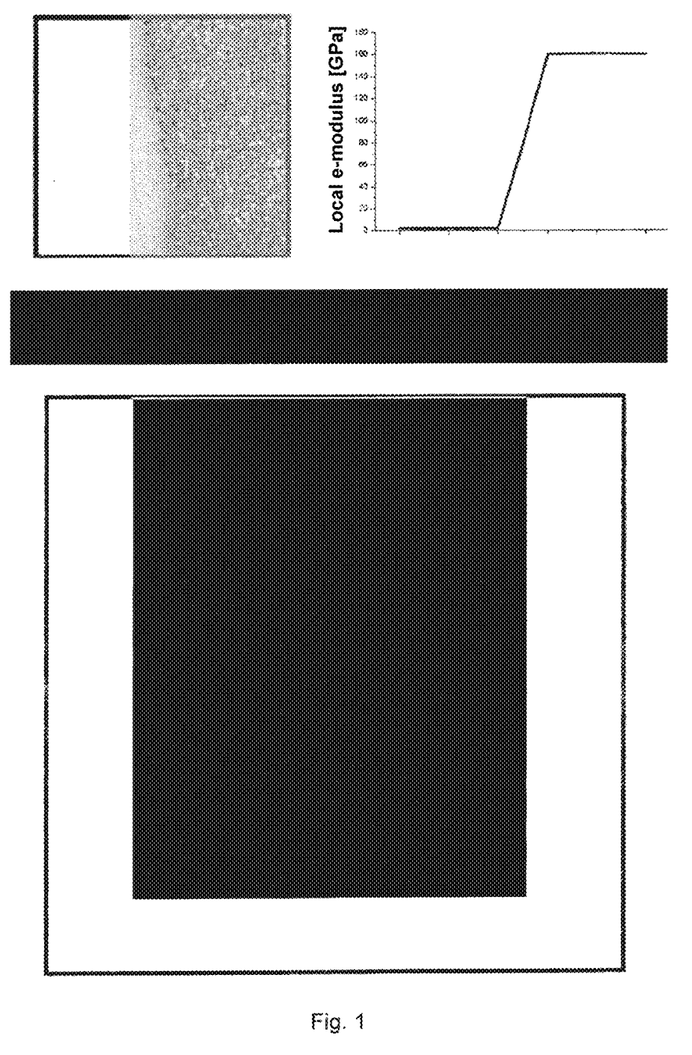
FIG. 1: Schematic representation of the connecting of two thermoplastics on the basis of a longitudinal section through the resulting implant preform; here consisting of two different PEEK compounds (material A and B); and schematic representation of the cross-sectional plane of the assembly zone of material A and B.

FIG. 1 shows schematically the outcome of this method on an exemplary basis, the materials employed here being a 10% titanium dioxide-filled PEEK as material A and a 30% carbon fiber-filled PEEK as material B. The materials used are characterized further as follows:

Material A: e.g., powder-filled PEEK with an elasticity modulus $E2=1-6$ GPa; here filled with $TiO_2$; PEEK with elasticity modulus $\geq 3$ GPa.

Material B: e.g. fiber-filled PEEK with an elasticity modulus $E8=50-160$ GPa; here PEEK filled 30% with short carbon fibers and with an elasticity modulus $\geq 20$ GPa.

In the microscope image of the cross-sectional plane through the connection of A+B, a seamless transition is observed between material A and B, it being possible for the walls of the materials to have a smooth and/or interlocking design. Graphically this can be illustrated by an elasticity modulus gradient within a sectional line through the region of the strong connection of material A and B.

Material A and B are based in principle on a thermoplastic, preferably PEEK, which may in each case be unfilled or filled homogeneously with different additives, resulting for A and B respectively in different mechanical properties and therefore different elasticity moduli, as defined above as E1-E8; here, the following ratios of material A elasticity modulus to material B elasticity modulus may come about, using two materials each with an elasticity modulus from the E1-E8 range: E-material B>1.1×E-material A, preferably in a ratio of E-material B>1.5-50×E-material A; over the course, as a result of the seamlessly interconnected plastics units, this results in different elasticity gradients occurring, so giving the resultant preform different material properties relative both to A alone and to B alone (see FIG. 1). In principle, if required, it is also possible for more than two materials to be joined durably to one another in this way, in which case it would be necessary to define a third base material as material C and a fourth base material as material D, and so on.

Application in Implantology

Figure 2:
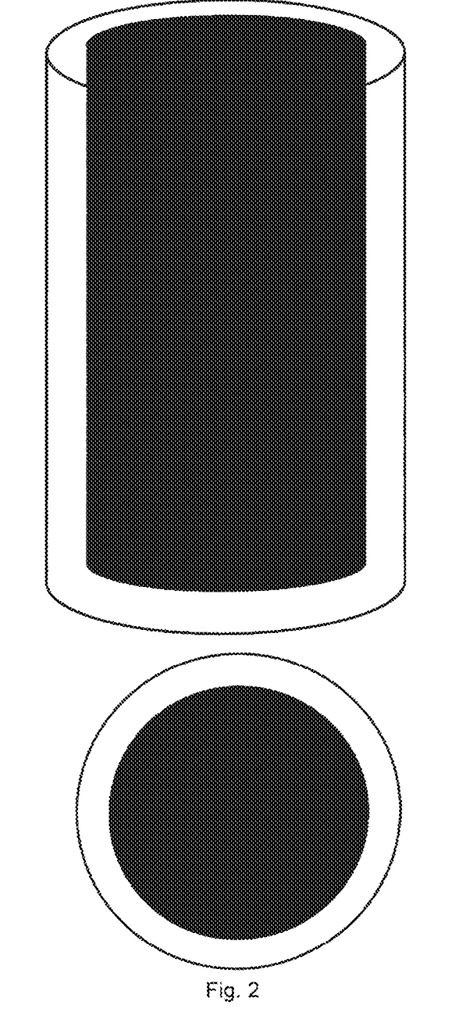
FIG. 2: Schematic representation of an implant preform as a basis for a dental implant in longitudinal aspect and as horizontal cross section.

FIG. 2 shows an implant preform produced in the manner described above and serving specifically for the production of a dental implant body, which can be further machined using CAD/CAM technology, for example, to give the completed medical product.

Thus FIG. 2 in a schematic representation (longitudinal aspect/horizontal cross section) shows an implant preform as a basis for a dental implant with a diameter of material B≥2 mm, preferably with an elasticity modulus in the E3-E8 range; with a seamless transition between material A and material B, it being possible for the walls of the materials in the assembly zone to have a smooth or interlock design.

The machining of the implant preform serving for production of a dental implant includes in particular the introduction of a central cavity, which is optionally lined with an internal thread, in order to ensure the fixing of an abutment post, optionally with a screw.

Figure 3:
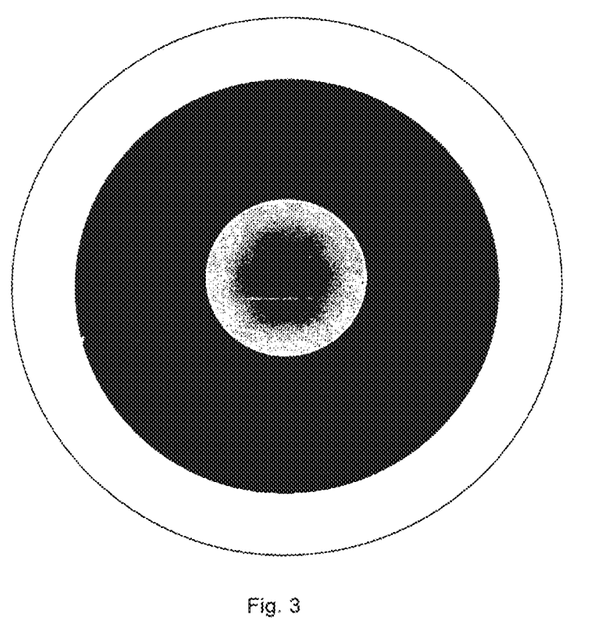
FIG. 3: Horizontal cross section through the body of a two-part dental implant.

FIG. 3 shows, schematically, the horizontal cross section through a dental implant of this kind. This FIG. 3 shows a seamless transition between material A and material B, and again the walls of the materials in the assembly zone may have a smooth or interlock design. The layer thickness of material A is 0.2 mm, preferably 0.5-1.5 mm, and there is preferably a material A having an elasticity modulus in the E1-E2 range. The diameter of material B is 2 mm, and preferably there is a material B having an elasticity modulus in the E3-E8 range. FIG. 3 also shows a central cavity in the direction of the longitudinal axis, which serves for the anchoring of a secondary component/abutment; in the case of anchoring by means of a central screw, there is an internal thread in the cavity for the fixing of the screw; the diameter of the central cavity is 0.9 mm, but still leaves a sufficient wall thickness of the material B.

Summary of the Results for Implant Preforms of the Invention and the Use or Further Processing a) Objectives achieved with the present invention:
through material combination, an elasticity modulus gradient from inside to outside is produced;
through stable core material, mechanically robust connection possibilities, by means of screwing (abutment fixing) in particular, are made possible;

through an elasticity modulus similar to the surrounding bone in the edge region, stress shielding is prevented;
through compounding of the outer material or shell material, bone integration can be ensured and optimized;
through compounding of the outer material or shell material, a colored design for improved esthetics can be achieved;
through compounding, x-ray-opacity is produced;
through 3D-model calculation, an optimized materials-related implant geometry is accomplished;

b) requirements for the combination of the materials A (shell) and B (core):
1. elasticity modulus of material A<elasticity modulus of material B;
2. homogeneous connection corresponding to a welded connection;
3. heterogeneous connection by adhesive bonding, use of adhesion promoters/bonders/adhesives, surface pre-treatment;
4. color design, with A always being lighter (white to tooth-colored) than B;
5. workability by thermoplastic shaping and/or machining;
6. materials combinations:
   inside (core)=material B: PEEK or other fiber-reinforced thermoplastics (primarily carbon fibers);
   outside (shell, jacket)=material A: injectable thermoplastic with high elasticity modulus, proven biocompatibility, and unfilled or filled with powder (hydroxylapatite, tricalcium phosphate, barium sulfate, titanium dioxide, zinc oxide, bioglasses), such as, for example: PA, PE, POM, PMMA, PVAc, PU, PEEK, PAEK.

c) Possible applications:
1. Dental Implant
   a) of homogeneous material
   b) of material with graded elasticity modulus In general a two-part dental implant has an outer thread which allows it to be rotated into the corresponding implant bearing in the bone. In its center there is usually an inner thread made, open toward the top, in order for the second part, the abutment post, to be fixed on the implant with a central screw, with the artificial substitute tooth being fixed in turn to the abutment. The joining region in which implant and abutment are in contact may have various designs. Preferably here a conical connection ought to be employed. The abutment in that case has a basal cone, which is inserted into the implant, with a total cone angle of 12°. The geometry of a dental implant body may have different dimensions, and the external diameter can be between 3.2 to 6 mm and the overall length between 6 to 18 mm. Testing was carried out on an implant with a 4 mm diameter and 8 mm length in the following 3 material versions:
Implant 1: made homogeneously of PEEK with approximately 10% $TiO_2$ filling (corresponding to material A); color: white;
Implant 2: made homogeneously from PEEK, reinforced with about 60% parallel continuous carbon fibers (corresponding to material B); color: black;
Implant 3: graded elasticity modulus (core: 3 mm diameter, PEEK reinforced with about 60% parallel carbon fibers; shell: 0.5 mm layer thickness, PEEK filled with about 10% $TiO_2$); color: white jacket, black core.

The implants were tested in a static pressure test in a universal testing machine. The compressive strength was determined from the results obtained from this pressure test. The compressive strengths were as follows:

Implant 1 (white): 140.1±1.3 MPa
Implant 2 (black): 712.7±66 MPa
Implant 3 (white jacket, black core): 610±24 MPa 2. Osteosynthesis Plate, or Bone Defect Bridging Plate for Oral, Maxillary, and Facial Surgery Through the production method of welding by friction (friction welding) it is also possible, for example, for two or more elements of the material B to be introduced permanently into a base form of the material A, in order thereby to form a stable abutment for screws. An implant preform of this kind is set out in FIG. 4, and may serve, for example, for reconstruction of defects in the bony cranium.

Figure 4:
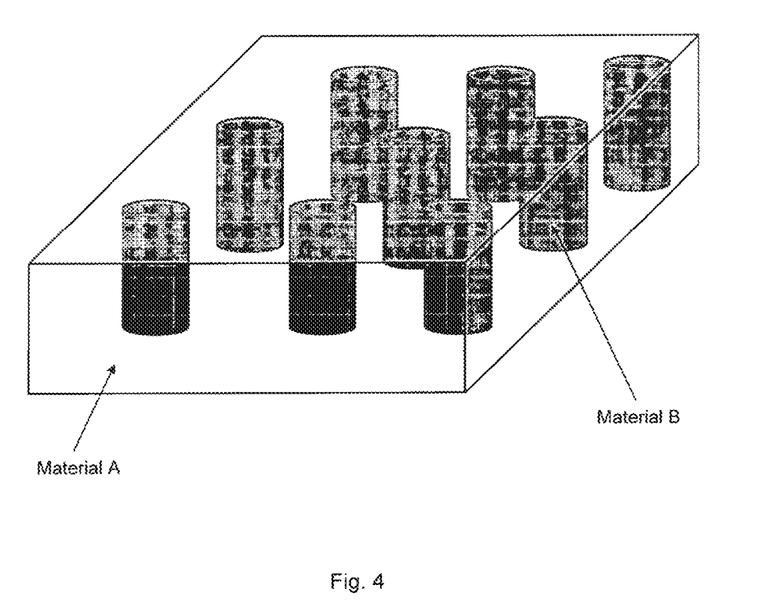
FIG. 4: Schematic representation for an implant preform as basis for the production of a plate for eliminating bone defects (bone reconstruction), the materials A and B being connected to one another as described in the preceding representations.

FIG. 4 here shows a schematic representation of an implant preform as a basis for the production of a plate for eliminating bone defects (bone reconstruction), with the materials A and B being connected seamlessly to one another as described in the preceding representations. The material A is, for example, PEEK with an elasticity modulus E1 or E2; the material B is, for example, PEEK with an elasticity modulus E3-E8.

The invention claimed is:
1. An implant preform comprising:
at least one external shell including a thermoplastic plastics unit (A) having an elasticity modulus EA and being configured, biocompatible and operative for direct implantation into bone for direct contact with bone without use of an intermediary device disposed between the external shell and bone; and
at least one internal core including a thermoplastic plastics unit (B) disposed in an interior of the at least one external shell and having an elasticity modulus EB;
wherein the elasticity modulus EA of the at least one external shell is similar to an elasticity modulus of bone and is less than the elasticity modulus EB;
wherein the biocompatible thermoplastic plastics unit (A) and the thermoplastic plastics unit (B) are seamlessly and thermally joined to one another in an assembly zone;
wherein the assembly zone has a decreasing elasticity modulus gradient from the elasticity modulus EB to the elasticity modulus EA adapted for maintaining a high mechanical strength of the implant preform while simultaneously reducing stress shielding effects upon direct implantation of the implant preform into bone of a subject for direct contact with bone without use of an intermediary device disposed between the external shell and bone.

2. The implant preform of claim 1, wherein the elasticity modulus EA of the thermoplastic plastics unit (A) is 1 to 6 GPa.

3. The implant preform of claim 1, wherein the elasticity modulus EB of the thermoplastic plastics unit (B) is 5 to 160 GPa.

4. The implant preform of claim 1, wherein the ratio of the elasticity modulus EA of the thermoplastic plastics unit (A) to the elasticity modulus EB of the thermoplastic plastics unit (B) is EA<1.1 EB.

5. The implant preform of claim 4, wherein the ratio of the elasticity modulus EA of the thermoplastic plastics unit (A) to the elasticity modulus EB of the thermoplastic plastics unit (B) is EA<1.1 to 50 EB.

6. The implant preform of claim 1, wherein the plastic in one or more of the plastics units, in each case independently of one another, is selected from the group consisting of PEEK, PA, PE, POM, PMMA, PVAc, PU, and PAEK.

7. The implant preform of claim 1, wherein the plastic of the thermoplastic plastics unit (A) is selected from the group consisting of PEEK, PA, PE, POM, PMMA, PVAc, PU, and PAEK.

8. The implant preform of claim 1, wherein the plastic of the thermoplastic plastics unit (B) is selected from the group consisting of PEEK or other thermoplastics.

9. The implant preform of claim 1, wherein the plastic in one or more of the plastics units, in each case independently of one another, is an additized plastic.

10. The implant preform of claim 1, wherein the plastic of the thermoplastic plastics unit (A) comprises additives in powder form.

11. The implant preform of claim 1, wherein the plastic of the thermoplastic plastics unit (B) is fiber-reinforced.

12. The implant preform of claim 1, wherein the plastics unit (A) is configured as external to the internal plastics unit (B).

13. The implant preform of claim 1, wherein the preform is configured for use as a dental implant.

14. The implant preform of claim 2, wherein the elasticity modulus EA of the thermoplastic plastics unit (A) is 2 to 5 GPa.

15. The implant preform of claim 2, wherein the elasticity modulus EA of the thermoplastic plastics unit (A) is 2.5 to 4.5 GPa.

16. The implant preform of claim 3, wherein the elasticity modulus EB of the thermoplastic plastics unit (B) is 20 to 150 GPa.

17. The implant preform of claim 3, wherein the elasticity modulus EB of the thermoplastic plastics unit (B) is 30 to 110 GPa.

18. The implant preform of claim 4, wherein the ratio of the elasticity modulus EA of the thermoplastic plastics unit (A) to the elasticity modulus EB of the thermoplastic plastics unit (B) is EA<1.5 EB.

19. The implant preform of claim 5, wherein the ratio of the elasticity modulus EA of the thermoplastic plastics unit (A) to the elasticity modulus EB of the thermoplastic plastics unit (B) is EA<1.5 to 50 EB.

20. The implant preform of claim 9, wherein the additized plastic comprises additives selected from the group consisting of reinforcing fibers, fillers, and pigments.

21. The implant preform of claim 20, wherein the reinforcing fibers are carbon fibers.

22. The implant preform of claim 20, wherein the fillers are selected from the group consisting of SiO2, BaSO4, tricalcium phosphate, tetracalcium phosphate, and bioglasses.

23. The implant preform of claim 20, wherein the pigments are TiO2.

24. The implant preform of claim 10, wherein the additives in powder form are selected from the group consisting of hydroxylapatite, tricalcium phosphate, barium sulfate, titanium dioxide, zinc oxide, and bioglasses.

25. The implant preform of any of claim 11, wherein the plastic of the thermoplastic plastics unit (B) is carbon fiber-reinforced.

26. The implant preform of claim 1 further comprising an anchoring portion within the at least one internal core for anchoring a secondary component.

27. The implant preform of claim 26, wherein the secondary component is an abutment.

28. The implant preform of claim 27, wherein the anchoring portion comprises an internal thread for fixing a corresponding screw.

29. An implant system comprising:
an implant preform comprising:
  at least one external shell including a thermoplastic plastics unit (A) having an elasticity modulus EA and being configured, biocompatible and operative for direct implantation into bone for direct contact with bone without use of an intermediary device disposed between the external shell and bone; and
  at least one internal core including a thermoplastic plastics unit (B) disposed in an interior of the at least one external shell and having an elasticity modulus EB;
    wherein the elasticity modulus EA of at the least one external shell is similar to an elasticity modulus of bone and is less than the elasticity modulus EB;
    wherein the thermoplastic plastics unit (A) and the thermoplastic plastics unit (B) are thermally joined to one another in an assembly zone;
    wherein a wall of the thermoplastic plastics unit (A) and a wall of the thermoplastics plastics unit (B) have a smooth design or an interlock design in the assembly zone; and
    wherein the assembly zone has a decreasing elasticity modulus gradient from the elasticity modulus EB to the elasticity modulus EA for maintaining a high mechanical strength of the implant preform while simultaneously reducing stress shielding effects upon direct implantation of the implant preform into bone of a subject for direct contact with bone without use of an intermediary device disposed between the external shell and bone;
  an anchoring portion disposed within the at least one core for anchoring a secondary component; and
  a secondary component.

30. The implant system of claim 29, wherein the anchoring portion comprises an internal thread for fixing a corresponding screw.

31. The implant system of claim 29, wherein the secondary component comprises an abutment.

32. The implant system of claim 31 further comprising an artificial substitute tooth being fixed to the abutment.

33. The implant system of claim 31, wherein the abutment comprises a basal cone, for insertion into the implant preform at a total cone angle of 12°.

34. A device for eliminating or reducing defects in a bone comprising:
a plate;
wherein the plate comprises a plurality of implant preforms;
wherein each of the plurality of implant preforms comprises:
at least one external shell including a thermoplastic plastics unit (A) having an elasticity modulus EA and being configured, biocompatible and operative for direct implantation into bone for direct contact with bone without use of an intermediary device disposed between the external shell and bone; and
at least one internal core including a thermoplastic plastics unit (B) disposed in an interior of the at least one external shell and having an elasticity modulus EB;
wherein the elasticity modulus EA of at the least one external shell is similar to an elasticity modulus of bone and is less than the elasticity modulus EB;
wherein the thermoplastic plastics unit (A) and the thermoplastic plastics unit (B) are thermally joined to one another in an assembly zone;

wherein a wall of the thermoplastic plastics unit (A) and a wall of the thermoplastics plastics unit (B) have a smooth design or an interlock design in the assembly zone; and wherein the assembly zone has a decreasing elasticity modulus gradient from the elasticity modulus EB to the elasticity modulus EA for maintaining a high mechanical strength of the implant preform while simultaneously reducing stress shielding effects upon implantation of the implant preform into bone of a subject for direct contact with bone without use of an intermediary device disposed between the external shell and bone.

* * * * *